(12) United States Patent
Parikh et al.

(10) Patent No.: US 7,939,105 B2
(45) Date of Patent: *May 10, 2011

(54) PROCESS FOR PREPARING A RAPIDLY DISPERSING SOLID DRUG DOSAGE FORM

(75) Inventors: Indu Parikh, Ile de Soeurs Verdun (CA); Awadhesh K. Mishra, Ile de Soeurs Verdun (CA); Robert Donga, Quebec (CA); Michael G. Vachon, Quebec (CA)

(73) Assignee: Jagotec AG, Muttenz (CH)

(*) Notice: Subject to any disclaimer, the term of this patent is extended or adjusted under 35 U.S.C. 154(b) by 0 days.

This patent is subject to a terminal disclaimer.

(21) Appl. No.: 09/443,863

(22) Filed: Nov. 19, 1999

(65) Prior Publication Data
US 2002/0106403 A1    Aug. 8, 2002

Related U.S. Application Data

(60) Provisional application No. 60/109,202, filed on Nov. 20, 1998.

(51) Int. Cl.
*A61K 9/14* (2006.01)
*A61K 9/16* (2006.01)

(52) U.S. Cl. ........ 424/490; 424/489; 424/491; 424/493; 424/494; 424/495; 424/496; 424/497; 424/498; 424/464; 424/468; 424/456; 424/457

(58) Field of Classification Search .......... 424/464–466, 424/489–502, 456, 457
See application file for complete search history.

(56) References Cited

U.S. PATENT DOCUMENTS

| | | | |
|---|---|---|---|
| 2,803,582 A | 8/1957 | Cherney |
| 3,137,631 A | 6/1964 | Soloway et al. |
| 3,185,625 A | 5/1965 | Brown |
| 3,216,897 A | 11/1965 | Krantz |
| 3,274,063 A | 9/1966 | Nieper et al. |
| 3,594,476 A | 7/1971 | Merrill |
| 3,715,432 A | 2/1973 | Merrill |
| 3,755,557 A | 8/1973 | Jacobs |
| 3,794,476 A | 2/1974 | Michalik et al. |
| 3,937,668 A | 2/1976 | Zolle |
| 3,960,757 A | 6/1976 | Morishita et al. |
| 3,965,255 A | 6/1976 | Bloch et al. |
| 4,016,100 A | 4/1977 | Suzuki et al. |
| 4,053,585 A | 10/1977 | Allison et al. |
| 4,056,635 A | 11/1977 | Glen et al. |
| 4,073,943 A | 2/1978 | Wretlind et al. |
| 4,078,052 A | 3/1978 | Papahadjopoulos |
| 4,089,801 A | 5/1978 | Schneider |
| 4,102,806 A | 7/1978 | Kondo et al. |
| 4,107,288 A | 8/1978 | Oppenheim et al. |
| 4,133,874 A | 1/1979 | Miller et al. |
| 4,145,410 A | 3/1979 | Sears |
| 4,147,767 A | 4/1979 | Yapel, Jr. |
| 4,186,183 A | 1/1980 | Steck et al. |
| 4,219,548 A | 8/1980 | Reller |
| 4,235,871 A | 11/1980 | Papahadjopoulos et al. |
| 4,241,046 A | 12/1980 | Papahadjopoulos et al. |
| 4,271,196 A | 6/1981 | Schmidt |
| 4,280,996 A | 7/1981 | Okamoto et al. |
| 4,298,594 A | 11/1981 | Sears et al. |
| 4,302,459 A | 11/1981 | Steck et al. |
| 4,308,166 A | 12/1981 | Marchetti et al. |
| 4,309,404 A | 1/1982 | DeNeale et al. |
| 4,309,421 A | 1/1982 | Ghyczy et al. |
| 4,316,884 A | 2/1982 | Alam et al. |
| 4,320,121 A | 3/1982 | Sears |
| 4,325,871 A | 4/1982 | Sasaki et al. |
| 4,328,222 A | 5/1982 | Schmidt |
| 4,329,332 A | 5/1982 | Couvreur et al. |
| 4,331,654 A | 5/1982 | Morris |
| 4,332,795 A | 6/1982 | Ghyczy et al. |
| 4,332,796 A | 6/1982 | Los |
| 4,340,594 A | 7/1982 | Mizushima et al. |

(Continued)

FOREIGN PATENT DOCUMENTS

| | | |
|---|---|---|
| DE | 2 513 797 | 10/1975 |
| DE | 2 938 807 | 11/1980 |
| DE | 3 421 468 | 12/1985 |
| DE | 4 440 337 | 5/1996 |
| EP | 0 052 322 | 5/1982 |
| EP | 0 272 091 | 6/1988 |
| EP | 0330532 A1 | 8/1989 |
| EP | 0 391 369 | 10/1990 |
| EP | 0 418 153 | 3/1991 |
| EP | 0 193 208 | 11/1991 |

(Continued)

OTHER PUBLICATIONS

Kawashima et al, "Preparation of Powdered Phospholipid Nanospheres...," Chem. Pharm. Bull., vol. 40, No. 7, pp. 1911-1916 (1992).

Freitas et al, "Spray-drying of solid lipid nanoparticles (SLN™)," European Journal of Pharmaceutics and Biopharmaceutics, vol. 46, pp. 145-151 (1998).

Ross et al., "Aqueous Solutions of Surface-Active Solutes", *Collodial Systems and Interfaces*, © 1988, pp. 148-151.

(Continued)

*Primary Examiner* — Gollamudi S Kishore
(74) *Attorney, Agent, or Firm* — Mintz Levin Cohn Ferris Glovsky and Popeo, P.C.; David E. Johnson; Muriel Liberto

(57) ABSTRACT

Rapidly dispersing solid dry therapeutic dosage form comprised of a water insoluble compound existing as a nanometer or micrometer particulate solid which is surface stabilized by the presence of at least one phospholipid, the particulate solid being dispersed throughout a bulking matrix. When the dosage form is introduced into an aqueous environment the bulking matrix is substantially completely dissolves within less than 2 minutes thereby releasing the water insoluble particulate solid in an unaggregated and/or unagglomerated state. The matrix is composed of a water insoluble substance or therapeutically useful water insoluble or poorly water soluble compound, a phospholipid and optionally also at least one non-ionic, anionic, cationic or amphipathic surfactant, together with a matrix or bulking agent and if needed a release agent. The volume weighted mean particle size of the water insoluble particle is 5 micrometers or less.

74 Claims, No Drawings

U.S. PATENT DOCUMENTS

| | | | |
|---|---|---|---|
| 4,345,588 A | 8/1982 | Widder et al. | |
| 4,351,831 A | 9/1982 | Growdon et al. | |
| 4,356,167 A | 10/1982 | Kelly | |
| 4,369,182 A | 1/1983 | Ghyczy et al. | |
| 4,371,516 A | 2/1983 | Gregory et al. | |
| 4,378,354 A | 3/1983 | Ghyczy et al. | |
| 4,394,372 A | 7/1983 | Taylor | |
| 4,397,846 A | 8/1983 | Weiner et al. | |
| 4,411,894 A | 10/1983 | Schrank et al. | |
| 4,411,933 A | 10/1983 | Samejima et al. | |
| 4,421,747 A | 12/1983 | Ghyczy et al. | |
| 4,427,649 A | 1/1984 | Dingle et al. | |
| 4,432,975 A * | 2/1984 | Libby | 424/201 |
| 4,440,514 A | 4/1984 | Keiter et al. | |
| 4,448,765 A | 5/1984 | Ash et al. | |
| 4,452,817 A | 6/1984 | Glen et al. | |
| 4,483,847 A | 11/1984 | Augart | |
| 4,485,054 A | 11/1984 | Mezei et al. | |
| 4,492,720 A | 1/1985 | Mosier | |
| 4,515,736 A | 5/1985 | Deamer | |
| 4,529,561 A | 7/1985 | Hunt et al. | |
| 4,532,089 A | 7/1985 | MacDonald | |
| 4,610,868 A | 9/1986 | Fountain et al. | |
| 4,613,505 A | 9/1986 | Mizushima et al. | |
| 4,622,219 A | 11/1986 | Haynes | |
| 4,629,626 A | 12/1986 | Miyata et al. | |
| RE32,393 E | 4/1987 | Wretlind et al. | |
| 4,675,236 A | 6/1987 | Ohkawara et al. | |
| 4,687,762 A | 8/1987 | Fukushima et al. | |
| 4,725,442 A | 2/1988 | Haynes | |
| 4,756,910 A | 7/1988 | Yagi et al. | |
| 4,758,598 A | 7/1988 | Gregory | |
| 4,761,288 A | 8/1988 | Mezei | |
| 4,762,720 A | 8/1988 | Jizomoto | |
| 4,766,046 A | 8/1988 | Abra et al. | |
| 4,776,991 A | 10/1988 | Farmer et al. | |
| 4,798,846 A | 1/1989 | Glen et al. | |
| 4,800,079 A | 1/1989 | Boyer | |
| 4,801,455 A | 1/1989 | List et al. | |
| 4,803,070 A | 2/1989 | Cantrell et al. | |
| 4,806,350 A | 2/1989 | Gerber | |
| 4,806,352 A | 2/1989 | Cantrell | |
| 4,826,687 A | 5/1989 | Nerome et al. | |
| 4,837,028 A | 6/1989 | Allen | |
| 4,839,111 A | 6/1989 | Huang | |
| 4,880,634 A | 11/1989 | Speiser | |
| 4,895,726 A | 1/1990 | Curtet et al. | |
| 4,961,890 A | 10/1990 | Boyer | |
| 4,963,367 A | 10/1990 | Ecanow | |
| 4,973,465 A | 11/1990 | Baurain et al. | |
| 4,990,337 A | 2/1991 | Kurihara et al. | |
| 5,030,453 A | 7/1991 | Lenk et al. | |
| 5,091,187 A | 2/1992 | Haynes | |
| 5,091,188 A | 2/1992 | Haynes | |
| 5,098,606 A | 3/1992 | Nakajima et al. | |
| 5,100,591 A | 3/1992 | Leclef et al. | |
| 5,145,684 A | 9/1992 | Liversidge et al. | |
| 5,154,930 A | 10/1992 | Popescu et al. | |
| 5,164,380 A * | 11/1992 | Carli | 524/58 |
| 5,169,847 A | 12/1992 | Nagy nee Kricsfalussy et al. | |
| 5,178,878 A | 1/1993 | Wehling et al. | |
| 5,179,079 A | 1/1993 | Hansen et al. | |
| 5,217,707 A | 6/1993 | Szabo et al. | |
| 5,246,707 A | 9/1993 | Haynes | |
| 5,272,137 A | 12/1993 | Blasé et al. | |
| 5,298,262 A | 3/1994 | Na et al. | |
| 5,302,401 A | 4/1994 | Liversidge et al. | |
| 5,304,564 A | 4/1994 | Tsuboi et al. | |
| 5,320,906 A | 6/1994 | Eley et al. | |
| 5,326,552 A | 7/1994 | Na et al. | |
| 5,336,507 A | 8/1994 | Na et al. | |
| 5,340,564 A | 8/1994 | Illig et al. | |
| 5,342,625 A | 8/1994 | Hauer et al. | |
| 5,346,702 A | 9/1994 | Na et al. | |
| 5,352,459 A | 10/1994 | Hollister et al. | |
| 5,360,593 A | 11/1994 | Bapatia | |
| 5,364,633 A | 11/1994 | Hill et al. | |
| 5,389,377 A | 2/1995 | Chagnon et al. | |
| 5,399,363 A | 3/1995 | Liversidge et al. | |
| 5,447,710 A | 9/1995 | Na et al. | |
| 5,461,039 A | 10/1995 | Tschollar et al. | |
| 5,470,583 A | 11/1995 | Na et al. | |
| 5,510,118 A | 4/1996 | Bosch et al. | |
| 5,527,537 A | 6/1996 | Dietl | |
| 5,545,628 A | 8/1996 | Deboeck et al. | |
| RE35,338 E | 9/1996 | Haynes | |
| 5,552,160 A | 9/1996 | Liversidge et al. | |
| 5,560,931 A | 10/1996 | Eickhoff et al. | |
| 5,569,448 A | 10/1996 | Wong et al. | |
| 5,571,536 A | 11/1996 | Eickhoff et al. | |
| 5,576,016 A | 11/1996 | Amselem et al. | |
| 5,578,325 A | 11/1996 | Domb et al. | |
| 5,589,455 A | 12/1996 | Woo | |
| 5,603,951 A | 2/1997 | Woo | |
| 5,631,023 A * | 5/1997 | Kearney | 426/465 |
| 5,635,210 A | 6/1997 | Allen, Jr. et al. | 424/465 |
| 5,637,625 A | 6/1997 | Haynes | |
| 5,639,474 A | 6/1997 | Woo | |
| 5,645,856 A | 7/1997 | Lacy et al. | |
| 5,656,289 A | 8/1997 | Cho et al. | |
| 5,660,854 A | 8/1997 | Haynes et al. | |
| 5,660,858 A | 8/1997 | Parikh et al. | |
| 5,662,932 A | 9/1997 | Amselem et al. | |
| 5,663,198 A | 9/1997 | Reul et al. | |
| 5,676,928 A | 10/1997 | Klaveness et al. | |
| 5,760,047 A | 6/1998 | Cincotta et al. | |
| 5,776,491 A | 7/1998 | Allen, Jr. et al. | |
| 5,776,495 A | 7/1998 | Duclos et al. | |
| 5,814,324 A | 9/1998 | Sato et al. | |
| 5,827,536 A | 10/1998 | Laruelle | |
| 5,827,541 A * | 10/1998 | Yarwood | |
| 5,827,822 A | 10/1998 | Floc'h et al. | |
| 5,834,025 A | 11/1998 | de Garavilla et al. | |
| 5,851,275 A | 12/1998 | Amidon et al. | |
| 5,858,398 A | 1/1999 | Cho | |
| 5,858,410 A | 1/1999 | Muller et al. | |
| 5,880,148 A | 3/1999 | Edgar et al. | |
| 5,891,469 A | 4/1999 | Amselem | |
| 5,891,845 A | 4/1999 | Myers | |
| 5,919,776 A | 7/1999 | Hagmann et al. | |
| 5,922,355 A * | 7/1999 | Parikh et al. | 424/489 |
| 5,932,243 A | 8/1999 | Fricker et al. | |
| 5,972,366 A | 10/1999 | Haynes et al. | |
| 5,976,577 A * | 11/1999 | Green | 424/490 |
| 6,028,054 A | 2/2000 | Benet et al. | |
| 6,045,829 A | 4/2000 | Liversidge et al. | |
| 6,046,163 A | 4/2000 | Stuchlik et al. | |
| 6,057,289 A | 5/2000 | Mulye | |
| 6,063,762 A | 5/2000 | Hong et al. | |
| 6,086,376 A | 7/2000 | Moussa et al. | |
| 6,096,338 A | 8/2000 | Lacy et al. | |
| 6,121,234 A | 9/2000 | Benet et al. | |
| 6,180,660 B1 | 1/2001 | Whitney et al. | |
| 6,193,985 B1 | 2/2001 | Sonne | |
| 6,228,399 B1 * | 5/2001 | Parikh et al. | 424/489 |
| 6,248,363 B1 | 6/2001 | Patel et al. | |
| 6,267,989 B1 | 7/2001 | Liversidge et al. | |
| 6,270,806 B1 | 8/2001 | Liversidge et al. | |
| 6,277,405 B1 | 8/2001 | Stamm et al. | 424/462 |
| 6,337,092 B1 | 1/2002 | Khan et al. | |
| 6,368,628 B1 | 4/2002 | Seth | |
| 6,375,986 B1 | 4/2002 | Ryde et al. | 424/489 |
| 6,387,409 B1 | 5/2002 | Khan et al. | |
| 6,465,016 B2 * | 10/2002 | Parikh et al. | 424/489 |
| 6,475,510 B1 * | 11/2002 | Venkatesh et al. | 424/441 |
| 6,534,088 B2 | 3/2003 | Guivarc'h et al. | |
| 6,589,552 B2 | 7/2003 | Stamm et al. | 424/457 |
| 6,604,698 B2 | 8/2003 | Verhoff et al. | |
| 6,652,881 B2 | 11/2003 | Stamm et al. | 424/462 |
| 6,682,761 B2 | 1/2004 | Pace et al. | |
| 6,696,084 B2 | 2/2004 | Pace et al. | |
| 7,255,877 B2 | 8/2007 | Parikh | |
| 2002/0003179 A1 | 1/2002 | Verhoff et al. | |
| 2002/0012675 A1 | 1/2002 | Jain et al. | |
| 2002/0012704 A1 | 1/2002 | Pace et al. | |
| 2002/0013271 A1 | 1/2002 | Parikh et al. | |

| | | | |
|---|---|---|---|
| 2002/0119199 | A1 | 8/2002 | Parikh |
| 2002/0161032 | A1 | 10/2002 | Guivarc'h et al. |
| 2008/0227763 | A1 | 9/2008 | Lanquetin et al. |

FOREIGN PATENT DOCUMENTS

| | | |
|---|---|---|
| EP | 0 456 670 | 11/1991 |
| EP | 0 456 764 | 11/1991 |
| EP | 0 499 299 | 8/1992 |
| EP | 0 330 532 | 12/1992 |
| EP | 0 570 829 | 11/1993 |
| EP | 0 580 690 | 2/1994 |
| EP | 0 601 618 | 6/1994 |
| EP | 0 602 700 | 6/1994 |
| EP | 0 605 497 | 7/1994 |
| EP | 0605497 A1 | 7/1994 |
| EP | 0 724 877 | 8/1996 |
| EP | 0 757 911 | 2/1997 |
| EP | 0839527 | 5/1998 |
| EP | 0914822 | 5/1999 |
| FR | 2 617 047 | 12/1988 |
| FR | 2819720 A1 | 7/2002 |
| GB | 1 527 638 | 10/1978 |
| GB | 2046094 | 11/1980 |
| GB | 2250197 A | 6/1992 |
| HU | 211 580 | 6/1995 |
| JP | 56167616 | 5/1980 |
| JP | 55141407 | 11/1980 |
| JP | 60174726 A | 9/1985 |
| JP | 60208910 | 10/1985 |
| JP | S62-22729 | 1/1987 |
| JP | 63502117 | 8/1987 |
| JP | 63233915 | 9/1988 |
| JP | 1-502590 | 7/1989 |
| WO | WO 8500011 | 1/1985 |
| WO | WO 8704592 | 8/1987 |
| WO | WO 88/04924 | 7/1988 |
| WO | WO-88/06438 A1 | 9/1988 |
| WO | WO 9104011 | 4/1991 |
| WO | WO 92/18105 | 10/1992 |
| WO | WO 93/05768 | 4/1993 |
| WO | WO 94/20072 | 9/1994 |
| WO | WO 95/11671 | 5/1995 |
| WO | WO-96/14830 A1 | 5/1996 |
| WO | WO 96/21439 | 7/1996 |
| WO | WO 96/24332 | 8/1996 |
| WO | WO 97/14407 | 4/1997 |
| WO | WO 97/38679 | 10/1997 |
| WO | WO 98/07414 | 2/1998 |
| WO | WO-98/30360 A1 | 7/1998 |
| WO | WO-98/31360 A1 | 7/1998 |
| WO | WO 98/41239 | 9/1998 |
| WO | WO 99/29300 | 6/1999 |
| WO | WO 99/29316 | 6/1999 |
| WO | WO-99/40904 A2 | 8/1999 |
| WO | WO-9948477 A1 | 9/1999 |
| WO | WO 99/49846 | 10/1999 |
| WO | WO 99/49848 | 10/1999 |
| WO | WO 99/61001 | 12/1999 |
| WO | WO 00/10531 | 3/2000 |
| WO | WO 00/30615 | 6/2000 |
| WO | WO 0030616 | 6/2000 |
| WO | WO 00/40219 | 7/2000 |
| WO | WO 00/41682 | 7/2000 |
| WO | WO-0050007 A1 | 8/2000 |
| WO | WO-00/51572 A1 | 9/2000 |
| WO | WO-00/76482 A1 | 12/2000 |
| WO | WO-01/03693 A1 | 1/2001 |
| WO | WO-0115688 A1 | 3/2001 |
| WO | WO-0121154 A2 | 3/2001 |
| WO | WO 01/30372 | 5/2001 |
| WO | WO-01/49262 A1 | 7/2001 |
| WO | WO-02/24169 A1 | 3/2002 |
| WO | WO-02/24193 A1 | 3/2002 |
| WO | WO-02/39983 A2 | 5/2002 |
| WO | WO-02/067901 A1 | 9/2002 |

OTHER PUBLICATIONS

Sande et al., "Antimicrobial Agents: Antifungal and Antiviral Agents", pp. 1219-1222.

Bittman, Robert, "Sterol-Polyene Antibiotic Complexation: Probe of Membrane Structure," *Lipids*, 1978, vol. 13, No. 10, pp. 686-691.

Mishra et al., "Scientifically Speaking: Novel Injectable Formulations of Water-Insoluble Drugs", *Controlled Release Newsletter*, vol. 17, Issue 2, Jun. 2000, pp. 21-30.

Bangham et al., "Diffusion of Univalent Ions Across the Lamellae of Swollen Phospholipids", *J. Mol. Biol.*, 1965, vol. 3, pp. 238-252.

Huang et al., "Interaction of the N-terminus of Sterol Carrier Protein 2 with Membranes: Role of Membrane Curvature", *Biochem. Journal*, 1999, vol. 8, pp. 593-603.

Gregoriadis, Gregory, "The Carrier Potential of Liposomes in Biology and Medicine", *New Engl. J. Med.*, 1976, vol. 295, No. 13, pp. 704-710.

Cudd et al., "Liposomes Injected Intravenously into Mice Associate with Liver Mitochondria," *Biochem. Biophys Acta,*, 1984, vol. 774, pp. 169-180.

Benz et al., "Electrical Capacity of Black Lipid Films and of Lipid Bilayers Made from Monolayers", *Biochem. Biophys. Acta*, 1975, vol. 394, pp. 323-334.

Goodman and Gillman's, "The Pharmacological Basis of Therapeutics," 7th Ed., *MacMillan Publishing Co.*, New York (1985), Chap. 15, p. 312.

Cherney, L.S., "Tetracaine Hydroiodide: A Long Lasting Local Anesthetic Agent for the Relief of Postoperative Pain", *Anesth. Analg.*, 1963, vol. 42, No. 4, pp. 477-481.

Haynes et al., "Metal-Ligand Interactions in Organic Chemistry and Biochemistry", B. Pullman and N. Goldblum (Eds.), part 2, 1977, pp. 189-212.

Haynes et al., "Ultra-Long Duration Local Anesthesia Produced by Injection of Lecithin-coated Methoxyflurane Microdroplets", *Anesthesiology*, 1985, vol. 63, No. 5, pp. 490-499.

Haynes et al., "Ultra-Long Duration Local Anesthesia Produced by Intra-Dermal Injection of Lecithin-Coated Methoxyflurane Microdroplets", *Proceed. Intern. Symp. Control. Rel. Bioact. Mater.*, 1987, vol. 14, pp. 293-294.

Kirkpatrick et al., "Local Anesthetic Efficacy of Methoxyflurane Microdroplets in Man," *Anesthesiology*, 1987, vol. 67(3A) p. A254.

Gennaro et al., (Eds.), "Sustained-Release Drug Therapy," *Remington's Pharmaceutical Sciences*, 1985, 17th Ed., p. 1645.

"Derived Diameters and Distribution Statistics," from an unknown web-site, 6 pages.

"Getting Started", Man 0106, Issue 1.0, *Malvern Instruments Ltd.*, England (Jan. 1996), pp. 7.1-7.7.

Chulia et al., (Eds.) "Powder Technology and Pharmaceutical Processes", Amsterdam (1994), pp. 66-67.

Herbert A. Leiberman and Leon Lachman, Eds., *Pharmaceutical Dosage Forms*, Tablets,1980, vol. 1, p. 13.

Miyajima, Koichiro, "Role of Saccharides for the Freeze-Thawing and Freeze-Drying of Liposome", *Advanced Drug Delivery Review*, 1997, vol. 24, pp. 151-159.

Buchmuller et al., "Cryopel: Ein neus Verfahren zum Pelletieren und Frosten Biologischer Substrate," *Gas Aktuell*, 1989, vol. 35, pp. 10-13.

Wu et al., "Pharmacokinetics of Methoxyflurane After Its Intra-Dermal Injection as Lecithin-Coated Microdroplets,"*Journal of Controlled Release*, 1989, vol. 9, pp. 1-12.

Pace et al., "Novel Injectable Formulations of Insoluble Drugs", *Pharmaceutical Technology*, Mar. 1999, vol. 23, No. 3, pp. 116-134.

Rompp'S Chemie Lexikon, (Dr. Hermann Rompp), "Emulsion", 2 Aufl., Bd. 1, Stuttgart (1950).

Bergmann, Ludwig, *Der Ultraschall*, 5 Aufl., 1949, Stuttgart, S. 551-564, 672f.

Lehninger, Albert L., "The Molecular Basis of Cell Structure and Function", *Biochemistry*, 1970, Chapter 10.

Guzman et al., "Formation and Characterization of Cyclosporine-Loaded Nanoparticles", *1088 J. Pharm. Sci.* 1993, vol. 82, No. 5, pp. 498-502.

Napper, Donald H., "Polymeric Stabilizations of Colloidal Dispersions", 1983.

Muller et al., Emulsions and Nanosuspensions, 1998, Chapter 9, p. 163.

Lourenco et al., "Steric Stabilization of Nanoparticles: Size and Surface Properties", *Int. J. of Pharm.*, 1996, vol. 138, pp. 1-12.

Luckham, Paul F., "The Physical Stability of Suspension Concentrates with Particular etc.", *Pestic. Sci.*, 1989, vol. 25, pp. 25-34.

Calvor et al., "Production of Microparticles by High-Pressure Homogenization", *Pharm. Dev. Tech.*, 1998, vol. 3(3), pp. 297-205.

Lafuma, Francoise, "The Role of Water-soluble Polymers at the Solid/Liquid Interface in the Mechanisms of Flocculation/Stabilizationof Aqueous Colloidal Suspensions", [LSP4]*La Fuma Polymery*, 1998, vol. 43, nr 2, pp. 104-108.

Website http://userpage.fu-berlin.de/~kayser/nanosuspensionen.htm.

Siekmann et al. ,"Melt-homogenized Solid Lipid Nanparticles Stabilized by the Non-ionic Surfactant Tyloxapol", *Pharm. Pharmacol Lett.*, 1994, vol. 3, pp. 225-228.

Muller et al., "Nanosuspensions for the I.V. Administration of Poorly Soluble Drugs-Stability During Sterilization and Long-Term Storage", *Dept. of Pharmaceutics, Biopharmaceutics and Biotechnology*, The Free University of Berlin, Kelchstraβe 31, D-12169 Berlin, Germany.

Zuidam et al., "Sterilization of Liposomes by Heat Treatment", *Pharmaceutical Research*, 1993,vol. 10, No. 11, pp. 1591-1596.

D. Fercej Temeljotov, et al., "Solubilization and Dissolution Enhancement for Sparingly Soluble Fenofibrate", Acta Pharm. 46 (1996) pp. 131-136.

J. Shepherd, "The Fibrates in Clinical Practice: Focus on Micronised Fenofibrate", Atherosclerosis 110 (Suppl.) (1994), S55-S63.

J.P. Guichard et al., "A Comparison of the Bioavailability of Standard or Micronized Formulations of Fenofibrate", Current Therapeutic Research, vol. 54, No. 5, Nov. 1993, pp. 610-614.

M-T. Sheu, et al., "Dissolution Studies of Fenofibrate in the Ethanolic Medium", The Chinese Pharmaceutical Journal, vol. 45, No. 1(1993), pp. 43-51.

Ellen et al., "Long-term Efficacy and Safety of Fenofibrate and a Statin in the Treatment of Combined Hyperlipidemic", Am. J. Cardiol., 81:60B-65B (1998).

"Grant and Hackh's Chemical Dictionary: 5th Edition" McGraw-Hill, Inc. p. 212.

Guichard et al., Curr. Med. Res.Opin., "A New Formulation of Fenofibrate: Suprabioavailable Tablets", 16(2):134-138 (2000).

Lieberman, Herbert and Leon Lachman, Eds., "Tablets", Pharmaceutical Dosage Forms, 1:13 (1980).

Luckham, P.F., "The Physical Stability of Suspension Concentrates with Particular Reference to Pharmaceutical and Pesticide Formulations," Pestic. Sci., 25:25-34 (1989).

Muller et al., "Nanosuspensions for the I.V. Administration of Poorly Soluble Drugs-Stability During Sterilization and Long-Term Storage," Int'l. Symp. Control. Rel. Bioact. Mat., 22:574-575 (1995).

"Phospholipon® 100H" Technical Data, American Lecithin Co., Oxford, CT.

"Phospholipon® 90H" Technical Data, American Lecithin Co., Oxford, CT.

"The Molecular Basis of Cell Structure and Function" in Lehninger Biochemistry, Chapter 10 (1970).

\* cited by examiner ic
PROCESS FOR PREPARING A RAPIDLY DISPERSING SOLID DRUG DOSAGE FORM This application claims the benefit of U.S. Provisional Application No. 60/109,202, filed Nov. 20, 1998, the entire content of which is hereby incorporated by reference in this application.

FIELD OF THE INVENTION

This invention relates to compositions comprised of water-insoluble or poorly soluble drug particles of a size of about 0.05 to 10 micrometers having a surface modifying agent or combination of agents, of which at least one is a phospholipid, adsorbed on to the surface thereof. The composition includes a matrix-forming agent(s) which is present in an amount sufficient to allow freeze-drying and subsequent release of the surface coated drug particles upon contact with an aqueous environment. Small surface coated particles are sometimes referred to as MicroCrystals (in U.S. Pat. Nos. 5,091,187 and 5,091,188), MicroParticles (WO 98/07414), NanoParticles (U.S. Pat. Nos. 5,145,684 and 5,302,401 and 5,145,684).

This invention further provides methods of making dried compositions of water-insoluble or poorly soluble drug particles having surface modifying agents or combinations of agents, of which at least one is a phospholipid, adsorbed on the surface thereof and matrix-forming agent(s). The matrix-forming agent(s) is present in an amount sufficient to allow freeze-drying, such as by lyophilization, with subsequent release of the surface coated drug particles upon contact with an aqueous environment. The method comprises contacting said phospholipid coated particle with the matrix-forming agent(s) for a time and under conditions sufficient to allow the phospholipid coated drug particles to be freeze-dried.

BACKGROUND OF THE INVENTION

Poor bioavailability of water insoluble compounds has long been a problem in the pharmaceutical and diagnostics industry. While compounds with an aqueous solubility of greater than 1% w/v are not expected to present dissolution-related bioavailability and absorption problems, many new chemical entities exhibit aqueous solubility much below this value (see Pharmaceutical Dosage Forms—Tablets, Vol 1, page 13, Edited by H. Lieberman, Marcel Dekker, Inc, 1980). Many highly useful compounds are dropped from development or are formulated in a manner otherwise undesirable due to poor water solubility. A great number of these compounds are unstable in aqueous media and some require dissolution in oil, rendering the dosage form often unpleasant to take or even painful to use via the parenteral route of administration. This can lead to poor patient compliance and potentially an overall greater expense in treatment due to unnecessary hospitalizations. It is therefore desirable to develop a formulation of these water insoluble compounds that can be dosed in the simplest possible form: a rapidly dispersing solid dosage form.

Many methods exist for preparing rapidly dispersing solid dosage medicaments. Traditional approaches to this problem have involved the dispersion of a biological active ingredient with pharmaceutically acceptable excipients using mix techniques and/or granulation techniques. Specific functional excipients known in the art can be employed to aid in liberating the medicament, as for example effervescent disintegration agents(s) as taught by U.S. Pat. No. 5,178,878.

As a method of improving the disintegration of the solid dosage form, thereby liberating the medicament, freeze drying techniques have been previously employed as described by U.S. Pat. Nos. 4,371,516; 4,758,598; 5,272,137. Additionally, spray drying techniques have been employed for similar purposes as for example, U.S. Pat. No. 5,776,491 which describes the use of a polymeric component, a solubilizing component and a bulking agent as a matrix forming composition upon spray drying. This particulate matrix rapidly disintegrates upon introduction to an aqueous environment to release the medicament. Although these approaches produce rapidly drug liberating solid dosage forms, they suffer from a number of disadvantages particularly with medicaments that are water insoluble or poorly water-soluble. In these cases, suspensions of water insoluble compounds are likely to sediment prior to completion of the freeze-drying or spray drying process leading to particle aggregation and potentially inhomogeneous dry dosage forms. Additionally, large macromolecules of polysaccharides, typified by dextrans, when utilized as matrix formers have been implicated in agglomeration tendencies in reconstituted freeze-dried suspensions of liposomes (Miyajima, 1997). Therefore, the proper selection and employment of saccharide matrix formers remains elusive, we believe it is linked to the surface physicochemical nature of the water insoluble particle under consideration.

Additionally, suspensions of water insoluble compounds will be subjected to unwanted particle size growth as a result of the process of Ostwald ripening. In order to curtail this process, stabilization of these micronized materials suspended in an aqueous environment can be achieved using compositions of a variety of pharmaceutically acceptable excipients known to those skilled in the art. Such approaches can be found, as example, in the commonly assigned U.S. Pat. Nos. 5,631,023 and 5,302,401 and EP0193208.

For instance, U.S. Pat. No. 5,631,023 discloses a method to prepare rapidly dissolving tablets (10 seconds) using Xantham gum at a maximum weight percent of 0.05 as the suspending and flocculating agent with gelatin in which are dispersed water insoluble drug particles. Mannitol is used as the preferred cryoprotectant. The suspension is freeze-dried in molds to generate the solid dosage form.

U.S. Pat. No. 5,302,401 describes a method to reduce particle size growth during lyophilization. It discloses a composition containing particles having a surface modifier adsorbed onto the surface together with a cryoprotectant, the cryoprotectant present in an amount sufficient to form a nanoparticle-cryoprotectant composition. A preferred surface modifier is polyvinylpyrrolidone, and a preferred cryoprotectant is a carbohydrate such as sucrose. Also described are methods of making particles having a surface modifier adsorbed on to the surface and a cryoprotectant associated with it. The patent refers specifically to 5% Danazol with 1.5% PVP and sucrose (2%) or mannitol (2%) as the cryoprotectant. Thus while various cyroprotectants are available and function adequately to protect the active agent during lyophilization, the solid product that results is often difficult to redisperse in aqueous media.

EP 0193208 describes a method of lyophilizing reagent-coated latex particles to allow for reconstitution without aggregation and discusses the need to incorporate a zwitterionic buffer such as an amino acid, a stabilizer such as PVP or bovine albumin and a cryoprotectant such as Dextran T10 or other polysaccharide.

SUMMARY OF THE INVENTION

This invention is directed to an improvement in the dispersibility of micronized particles through the specific selection of excipients and methodology necessary to recover the primary particles. Inherent in this approach is the ability to produce stable aqueous suspensions of micron or submicron sized particles of water insoluble or poorly water-soluble compounds. These particles, which are required in the practice of the present invention, can be prepared according to the methods disclosed in U.S. Pat. Nos. 5,091,187 and 5,091,188 as well as WO 98/07414, whose disclosure is incorporated herein by reference. Briefly, water insoluble or poorly soluble compounds are dispersed in an aqueous medium in the presence of surface modifying agents or combinations of agents of which at least one is a phospholipid adsorbed on the surface thereof. Particle fragmentation occurs when the aforementioned suspension is subjected to stress as a result of processing with the use of various methods known in the art including, but not limited to, sonication, milling, homogenization, microfluidization, and antisolvent and solvent precipitation. The particle so produced is referred to as a microparticle which is defined herein as a solid particle of irregular, nonpherical or spherical shape having a nominal diameter of from nanometers to micrometers on to which is adsorbed a least one surface modifying agent of which one is a phospholipid.

According to this invention the microparticle suspension so produced is further admixed with surface modifying agent(s) and/or matrix-forming agent(s) which are present in an amount sufficient to allow freeze-drying and subsequent release of the surface coated drug particles upon contact with an aqueous environment. The selection of these components serves to minimize the tendency of microparticles to aggregate upon drying. Such aggregates are extremely difficult to redisperse due to the very high particle surface area which facilitates the degree of contact available to interacting particles resulting in irreversible lattices.

Small particle sizes of drugs are often needed in drug formulation development in order to maximize surface area, bioavailability, and dissolution requirements. The introduction of a suitable matrix-forming agent(s) in the above noted process serves to stabilize the phospholipid coated drug particle during the freeze-drying process and in the resulting freeze-dried product by suppressing any tendency of particle agglomeration or particle growth.

DESCRIPTION OF THE INVENTION

The present invention provides a rapidly disintegrating solid dosage form for water insoluble compounds, which releases primary particles stabilized with one or more surface modifiers, including but not limited to phospholipids. Examples of some preferred water-insoluble drugs include antifungal agents, immunosuppressive and immunoactive agents, antiviral agents, antineoplastic agents, analgesic and anti-inflammatory agents, antibiotics, antiepileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and, antarrhythmics, antihypertensive agents, hormones, and nutrients. A detailed description of these drugs may be found in Remington's Pharmaceutical Sciences, 18th Edition, 1990, Mack Publishing Co., PA. The concentration of the water insoluble ingredient in the aqueous suspension can vary between 0.1% w/w and 60% w/w, preferably between 5% w/w and 30% w/w.

The water insoluble compound is first prepared as an aqueous suspension in the presence of one or more surface stabilizing agents, of which at least one is a phospholipid. The phospholipid may be any natural or synthetic phospholipid, including but not limited to, phosphatidylcholine, phosphatidylethanolamine, phosphatidylserine, phosphatidylinoistol, phosphatidylglycerol, phosphatidic acid, lysophospholipids, egg or soybean phospholipid or a combination thereof. The phospholipid may be salted or desalted, hydrogenated or partially hydrogenated or natural, semisynthetic or synthetic. The concentration of the phospholipid ingredient in the aqueous suspension can vary between 0.1% w/w and 90% w/w, preferably between 0.5% w/w and 50% w/w and more preferably between 1% w/w and 20% w/w.

Examples of some suitable second and additional surface modifiers include: (a) natural surfactants such as casein, gelatin, natural phospholipids, tragacanth, waxes, enteric resins, paraffin, acacia, gelatin, and cholesterol, (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inositol, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylammonium bromide, and lauryldimethylbenzyl-ammonium chloride, (e) colloidal clays such as bentonite and veegum. A detailed description of these surfactants may be found in Remington's Pharmaceutical Sciences, 18th Edition, 1990, Mack Publishing Co., PA; and Theory and Practice of Industrial Pharmacy, Lachman et al., 1986. The concentration of additional surfactants in the aqueous suspension can vary between 0.1% w/w and 90% w/w, preferably between 0.5% w/w and 50% w/w and more preferably between 1% w/w and 20% w/w. These surfactants may be either added initially during compounding or added post processing prior to freeze-drying or a combination of both depending on the nature, concentration and number of the surfactant(s).

The resulting coarse dispersion is primarily intended to distribute the surfactant(s) throughout the aqueous medium using traditional mixing methods involving shear, extrusion, agitation and/or cavitation. The coarse dispersion is referred to as a pre-mix for purposes of this disclosure.

The premix is then subjected to a process which facilitates particle fragmentation including but not limited to sonication, milling, homogenization, microfluidization, and antisolvent and solvent precipitation. The attrition time may vary and is dependent on the physicochemical characteristics of the medicament, the physicochemical characteristics of the surfactant(s) and the selected attrition process. As an example, high pressure homogenization processes can be employed as typified by the use of equipment such as APV Gaulin E15, Avestin C50 or MFIC Microfluidizer M110EH. In this process, the particles in the premix are reduced in size at a pressure and temperature which does not significantly compromise the stability of the medicament and/or the surfactant(s). Processing pressures of about 2000 psi to 30,000 psi, preferably of about 5,000 psi to 20,000 psi, more preferably of about 10,000 psi to 18,000 psi and operating temperatures of about 2° C. to 65° C., more preferably 10° C. to 45° C. are suitable. The processing fluid is cycled through the homogenization chamber in such a manner as to ensure the entire fluid admixture is subjected to discrete homogenization resulting in a homogeneous suspension of micron or submicron particles. The mean volume weighted particle size of the resulting suspended therapeutic agent is measured to be between 0.05 micrometers to 10 micrometers, preferably between 0.2 micrometers to 5 micrometers using a laser light diffraction based instrument, Malvern Mastersizer Microplus.

The resulting homogeneous suspension of microparticles stabilized by one or more surface modifiers is then mixed with matrix-forming bulking and/or releasing agents (dry or as an aqueous solution) and is then dried. The bulking or matrix-forming agent provides a mass in which the particles of drug are embedded or retain. The release agent assists in disintegration of the matrix when it contacts aqueous media. The bulking/releasing agents are chosen in order to produce a support matrix that, upon drying, will yield rapidly dispersible tablets that release the primary particles upon reconstitution in an aqueous medium. Examples of matrix-forming agents include (a) saccharides and polysaccharides such as mannitol, trehalose, lactose, sucrose, sorbitol, maltose; (b) humectants such as glycerol, propylene glycol, polyethylene glycol; (c) natural or synthetic polymers such as gelatin, dextran, starches, polyvinylpyrrolidone, poloxamers, acrylates; (d) inorganic additives such as colloidal silica, tribasic calcium phosphate and; (e) cellulose based polymers such as microcrystalline cellulose, hydroxymethyl cellulose, hydroxypropyl cellulose, and methylcelluloses. Matrix forming agents may be added prior to producing the micronized particles of the therapeutic agent (formulation) or to the homogeneous suspension of microparticles prior to freeze-drying. The concentration of the matrix forming agents in the aqueous suspension can vary between 0.1% w/w and 90% w/w, preferably between 0.5% w/w and 50% w/w and more preferably between 1% w/w and 20% w/w.

The prepared aqueous suspension can be dried using several methods well known in the art. Spray drying, spray coating and freeze-drying are among the most common methods. The examples cited in Table 1 all use freeze drying as the drying method but this is not intended to be in any way limiting. The preferred method of freeze-drying is by lyophilization involving the sublimation of the frozen water from the aqueous suspension medium under reduced pressure. Lyophilization of this suspension may be performed in suitable containers such as glass vials, open trays, unit dosage form molds or in-situ spraying onto a supporting matrix. By way of example of the lyophilization process, the prepared suspension of microparticles containing matrix forming agents is distributed into stainless steel trays which are placed onto pre-equilibrated shelves held at a temperature of 5° C. within a pressure rated, sealed chamber. The prepared suspension is then subjected to decreasing temperature at a rate of 5° C./min to −50° C. until all of the suspension medium is completely solidified. This procedure uses only moderate temperature gradients because of the energy losses between different boundaries (shelf-tray-liquid). As a general rule, the typical time for freezing a 1 cm layer of a dilute aqueous suspension is 40-90 min at a temperature of −50° C. Freezing outside of the lyophilization chamber may also be accomplished by: (a) freezing on cooled plates, e.g., in trays or in the form of small particles on a drum cooler, (b) dropping in liquid nitrogen or some other cooling liquid, (c) co-spraying with liquid $CO_2$ or liquid nitrogen, or (d) freezing with circulating cold air.

Separate cooling is necessary for the performance of continuous freeze-drying. Equipment producing small pellets by dropping the solution into liquid nitrogen is commercially available as the Cryopel® process (Buchmuller and Weyermanns, 1990). Direct freezing inside the lyophilization chamber is advantageous if the product requires handling under aseptic conditions as may be the situation in the preparation of injectable dried formulations.

The so-obtained solidified prepared suspension is held at this temperature for a period of 2 hours to ensure all crystallization has been completed. The pressure inside the chamber is reduced to a pressure of approximately 5 mm of Hg and preferably to about 0.1 mm Hg. The sublimation of the frozen water is accomplished by raising the shelf temperature of the lyophilizer to about −30° C. to −10° C. and holding the material at this temperature for about 20 hours until the primary drying stage is completed. The drying time depends on a number of factors, some of them fairly constant and can be approximated as the heat of sublimation of ice, thermal conductivity of the frozen suspension and, the mass transfer coefficient. Other factors such as temperature or pressure in the chamber may vary considerably. The temperature of the shelves may be further increased to effect secondary drying as deemed necessary according to the composition of the sample.

Material is harvested from the lyophilizing cycle upon returning the chamber to ambient conditions. The harvested dried material may be passed through a coarse milling operation to facilitate handling or further blending operations with other excipients necessary to complete the required solid dosage form. These may include tableting aids for compression, glidants for hard gelatin encapsulation or dispersants for dry powder inhalers.

The matrix-forming agent used in the present invention must dissolve or disperse upon contact with an aqueous environment and release the phospholipid coated therapeutic agent particle. Upon reconstitution, the product reverts to a suspension having the same degree of dispersity as the pre-dried suspension, with preferably no more than 20% by weight and more preferably no more than 10% by weight and ideally less than 1% by weight of aggregated primary particles as revealed by the particle sizing and microscopic methods known in the art. Surprisingly, the freeze-dried suspension prepared according to the present invention can be stored for extended periods of time, even at high temperature and humidity, without loss of this redispersibility characteristic upon reconstitution and thus is essentially devoid of particle aggregation. Freeze-dried suspensions prepared in accordance with the composition of Examples 6-10 herein can be stored for at least 60 days at room temperature indicating the possibility of long term storage consistent with pharmaceutical dosage form shelf life.

Solid dosage material prepared according to the present invention is defined as possessing the characteristic of being rapidly dispersible. This characteristic is identified as the time required for the complete disintegration of a freeze-dried cake arising from this invention when subjected to an aqueous medium as occurs upon administration of the dosage form to in-vivo systems. Disintegration time can be measured by carrying out an in-vitro test such as observing the disintegration time in water at 37° C. The dosage material is immersed in the water without forcible agitation whereupon the time required for the material to substantially disperse by observation is noted. In the context of the definition of "rapid", the disintegration time is expected to be less than 2 minutes and preferably less than 30 seconds and most preferably less than 10 seconds.

The rate of dissolution or release of the active ingredient may also be affected by the nature of the medicament and the microparticle composition such that it may be rapid (5-60 sec) or intermediate (on the order of 75% disintegration in 15 minutes) or sustained-released.

In some cases, visual microscopic observation or scanning electron micrographs may reveal the presence of aggregates of particles however these particles are small in size and consist of aggregates of the original pre-freeze dried suspension particles. These aggregates are easily dispersed by low levels of energy such as short periods of sonication or physical agitation and as such display the key feature of this invention i.e. the prevention of particle size growth and irreversible aggregation and/or agglomeration.

EXAMPLES

The present invention of a rapidly dispersing, solid medicament is illustrated by way of the examples summarized in Table 1. Compositions noted in this table are expressed on % weight basis of the dried product. It is understood that the bulking agent may be added to the suspension prior to the homogenization step or prior to the drying step.

reconstitute favorably when traditional freeze drying cryoprotectants such as lactose or PVP 17 are used as described in U.S. Pat. No. 5,302,401. For these examples, large aggregates are formed comprised of adhering primary particles.

Examples 6 to 10 illustrate that the original suspension particle is easily and rapidly recovered upon reconstitution of the dried powder requiring no excessive agitation. These examples require careful selection of the bulking agent which may also act as a cryoprotectant as well as a humectant, such as, trehalose in formulation 8 and mannitol in formulation 10.

Alternatively, when a single matrix forming bulking agent is not suitable, as in the case of sucrose, the composition may include a mixture of bulking agents selected from pharmaceutically acceptable agents such as sucrose, trehalose, mannitol, sorbitol, or lactose. Example formulations 6, 7, and 9 demonstrate this type of composition. Volume weighted particle size distribution profiles of fenofibrate formulation 6 are shown in FIGS. 6 and 7, respectively, before and after the lyophilization/reconstitution step. This example demon-

TABLE 1

Composition (% w/w) and Attributes of Solid Dosage Form Examples

| Formulation Number | Phospholipids | | Additional Surfactants | | | | Active Ingredient | | | Bulking Agent | | | | Attributes | | |
|---|---|---|---|---|---|---|---|---|---|---|---|---|---|---|---|---|
| | | | Myrj 52 | PVP17 | NaDeox | Tween 80 | CyA | ITR | FEN | Type | Qty | Type | Qty | Disintegration Time (sec) | Particle Size pre-Lyo (micron) | Particle Size post-Lyo (micron) |
| | E80 | P100H | | | | | | | | | | | | | | |
| 1 | — | — | — | — | — | — | 33 | — | — | LAC | 67 | — | — | 5 | 10.6 | 13.3 |
| 2 | — | — | — | — | — | — | 62.5 | — | — | PVP17 | 37.5 | — | — | 5 | 10.2 | 17.4 |
| 3 | — | — | 4.6 | — | 1.1 | — | 23 | — | — | MAN | 5.5 | LAC | 46 | 60 | 0.66 | 48.9 |
| 4 | 23.1 | — | — | — | — | — | — | — | 76.9 | — | — | — | — | >2 min. | 0.91 | 85.50 |
| 5 | — | 5.6 | — | — | — | 5.6 | — | — | 27.8 | MAN | 61.0 | — | — | 10 | 0.97 | 6.73 |
| 6 | 9.1 | — | — | — | — | — | — | — | 33.3 | SUC | 45.5 | SOR | 15.1 | 5 | 0.97 | 0.98 |
| 7 | 11.1 | — | — | — | — | — | — | 27.8 | — | TRE | 33.3 | LAC | 27.8 | 5 | 1.15 | 1.15 |
| 8 | 15.4 | — | — | — | — | — | — | 38.4 | — | TRE | 46.2 | — | — | 5 | 1.15 | 1.12 |
| 9 | — | 8.4 | 4.2 | — | 1.0 | — | 21.1 | — | — | MAN | 23.2 | LAC | 42.1 | 15 | 0.92 | 1.33 |
| 10 | — | 11.9 | 6.0 | 17.9 | 1.5 | — | 29.9 | — | — | MAN | 32.8 | — | — | 5 | 0.91 | 1.08 |

Symbols and Note:
CyA = Cyclosporine;
E80 = Lipoid E80;
FEN = Fenofibrate;
ITR = Itraconazole;
MAN = Mannitol;
NaDeox = Sodium deoxycholate;
P100H = Phospholipon 100H;
PVP17 = Polyvinyl pyrrolidone;
SOR = Sorbitol;
SUC = Sucrose;
TRE = Trehalose Formulations 1 and 2 as show in the above table illustrate that reconstitutable particulates are obtained from these compositions, indicating that the relatively large size of the particulates (approximately 10 micrometers) poses little problem from an aggregation perspective. These relatively large particulates are easily achieved by traditional particle fracturing techniques. However, in order to appreciably affect bioavailability, particles which are an order of magnitude less in size are required. These particulates are obtained using procedures described in U.S. Pat. Nos. 5,091,187 and 5,091,188 as Microcrystals, WO 98/07414 as microparticles, and U.S. Pat. Nos. 5,145,684, 5,302,401 and 5,145,684 as nanocrystals. It is the particulates arising from these compositions that require specific excipient selection and processing conditions in order to recover the original suspension particle. Examples 3 to 5 illustrate that certain microparticle compositions do not strates the ideal scenario of no change in the particle size distribution profile following lyophilization and reconstitution.

With no intention to propose any particular theoretical explanation, it may be speculated that the components of the bulking agent mixture may simultaneously serve to inhibit the particle size increase on lyophilization/reconstitution by one or more mechanisms including cryoprotection, humectant action, dispersibility, and others.

These criteria are surprisingly important considerations when attempting to recover the unaggregated particulate suspension following reconstitution of a dried dosage form that comprises a phospholipid as one of the surface stabilizers.

In addition to the example compositions mentioned above, the formulations of this invention may additionally contain suitable amounts of pH buffering salts and pH adjusting agents such as sodium hydroxide and/or pharmaceutically acceptable acids. It is known to those skilled in the chemistry of phospholipids that at pH lower than 4 and higher than 10 the phospholipid molecules undergo extensive hydrolysis. Therefore, the pH of the suspension is usually adjusted to within this range prior to homogenization. If necessary the pH can be readjusted prior to the drying step.

While the invention and the examples have been described in connection with what is presently considered to be the most practical and preferred embodiment, it is to be understood that the invention is not to be limited to the disclosed embodiments, but on the contrary, is intended to cover various modifications and equivalent arrangements included within the spirit and scope of the following claims.

We claim:

1. A process for the preparation of a rapidly disintegrating solid dosage form capable of forming a stable suspension without irreversible particle aggregation, particle agglomeration, or particle growth, comprising the steps of:
    a) preparing an aqueous suspension including primary particles of a water insoluble or poorly water-soluble drug in the presence of one or more surface stabilizing agents, of which at least one is a phospholipid, or a combination of one or more surface stabilizing agents and one or more phospholipids, wherein the concentration of the phospholipid in the aqueous suspension ranges from about 0.1% w/w to about 90% w/w;
    b) subjecting the aqueous suspension to a particle fragmentation process to form a homogeneous aqueous suspension of micron and submicron particles, wherein the mean volume weighted particle size of the water-insoluble or poorly water-soluble drug particles in the suspension ranges between about 0.05 and about 10 micrometers;
    c) admixing the homogenous suspension of step b) with at least two rapidly dispersible matrix-forming agents said at least two rapidly dispersible matrix-forming agents, being present in an amount of between 0.1% w/w and 90% w/w of the aqueous suspension, said amount permitting a dried solid form of said suspension, upon reconstitution in an aqueous environment, to revert to a suspension having no more than about 20% by weight of particle aggregation or agglomeration compared with the amount of aggregation or agglomeration of particles comprising a pre-dried suspension;
    d) drying the admixture to produce a solid having surface stabilized drug particles dispersed and embedded throughout a support matrix formed by the at least two matrix-forming bulking/releasing agents, or combination thereof, wherein the support matrix dissolves or substantially disperses in a rapid disintegration time of less than 2 minutes upon contact between the solid and aqueous environment resulting in a release of the surface stabilized drug particles into the aqueous environment as a suspension; and further wherein, after contact between the solid and the aqueous environment, the resulting suspension comprises no more than about 20% by weight of aggregated or agglomerated primary particles;
    e) course milling and blending the solid with one or more pharmaceutically acceptable excipients to produce a dried powder; and
    f) forming the solid or dried powder into a solid dosage form of the drug.

2. The process according to claim 1, wherein the at least two matrix-forming agents are selected from the group consisting of a pharmaceutically acceptable saccharide, a pharmaceutically acceptable polysaccharide, a pharmaceutically acceptable humectant, a pharmaceutically acceptable cellulose based polymer, combinations thereof, and combinations of these with a pH buffering salt.

3. The process according to claim 1, wherein the at least two matrix-forming agents are selected from the group consisting of mannitol, trehalose, sorbitol, maltose, sucrose, lactose and combinations thereof; combinations of mannitol, trehalose, sorbitol and maltose with lactose; combinations of mannitol, trehalose, sorbitol, maltose, and lactose with sucrose; microcrystalline cellulose, hydroxymethyl cellulose, hydroxypropyl cellulose, methylcellulose and combinations thereof; and combinations thereof with a pH buffering salt.

4. The process according to claim 1, wherein the at least two matrix-forming agents are present in an amount between 0.5% w/w and 50% w/w of the aqueous suspension.

5. The process according to claim 1, wherein the water-insoluble or poorly water-soluble drug is selected from the group consisting of antifungal agents, immunosuppressive agents, immunoactive agents, antiviral agents, antineoplastic agents, analgesic agents, anti-inflammatory agents, antibiotic agents, antiepileptic agents, anesthetic agents, hypnotic agents, sedative agents, antipsychotic agents, neuroleptic agents, antidepressant agents, anxiolytic agents, anticonvulsant agents, antagonist agents, neuron blocking agents, anticholinergic agents, cholinomimetic agents, antimuscarinic agents, muscarinic agents, anti adrenergic agents, antiarrhythmic agents, antihypertensive agents, hormones, and nutrients.

6. The process according to claim 1, wherein the drug is selected from the group consisting of fenofibrate, itraconazole, and cyclosporine.

7. The process according to claim 1, wherein the drug is present in an amount between 0.1% w/w and 60% w/w of the aqueous suspension.

8. The process according to claim 1, wherein the phospholipid is selected from the group consisting of an egg phospholipid, a soybean phospholipid, and combinations thereof.

9. The process according to claim 1, wherein the phospholipid is selected from the group consisting of hydrogenated phospholipid, partially hydrogenated phospholipid, and combinations thereof.

10. The process according to claim 1, wherein the phospholipid is selected from the group consisting of phosphatidylcholine, phosphatidylethanolamine, phosphatidylserine, phosphatidylinositol, phosphatidylglycerol, phosphatidic acid, a lysophospholipid, and combinations thereof.

11. The process according to claim 1, wherein the surface stabilizing agent is selected from the group consisting of pharmaceutically acceptable nonionic surfactants, pharmaceutically acceptable anionic surfactants, and pharmaceutically acceptable cationic surfactants.

12. The process according to claim 1, wherein the surface stabilizing agent is selected from the group consisting of casein, gelatin, tragacanth, acacia, and combinations thereof.

13. The process according to claim 1, wherein the surface stabilizing agent is selected from the group consisting of a pharmaceutically acceptable polyoxyethylene fatty alcohol ether, a sorbitan fatty acid ester, a polyoxyethylene fatty acid ester, a poloxamer, a polaxamine, and combinations thereof.

14. The process according to claim 1, wherein the surface stabilizing agent is selected from the group consisting of glycerol monostearate, cetyl alcohol, cetostearyl alcohol, stearyl alcohol, and combinations thereof.

15. The process according to claim 1, wherein the surface stabilizing agent is selected from the group consisting of potassium laurate, triethanolamine stearate, sodium lauryl sulfate, an alkyl polyoxyethylene sulfate, sodium alginate, sodium deoxycholate, dioctyl sodium sulfosuccinate, a negatively charged glyceryl ester, sodium carboxymethylcellulose, calcium carboxymethylcellulose, and combinations thereof.

16. The process according to claim 1, wherein the surface stabilizing agent is selected from the group consisting of benzalkonium chloride, cetyltrimethylammonium bromide, lauryldimethylbenzylammonium chloride, and combinations thereof.

17. The process according to claim 1, wherein the surface stabilizing agent is present in an amount between 0.5% w/w and 50% w/w of the aqueous suspension.

18. The process according to claim 1, wherein the admixture is dried by spray drying, spray coating, or freeze-drying.

19. The process according to claim 1, wherein the particle fragmentation process is selected from the group consisting of sonication. milling, homogenization, microfluidization, antisolvent precipitation and solvent precipitation.

20. The process according to claim 1, wherein the pharmaceutically acceptable excipient is a tableting aid for compression, a glidant for hard gelatin encapsulation, aneffervescent disintegration agent, a dispersant for a dry powder inhaler, or a combination thereof.

21. The process according to claim 1, wherein the dosage form is a tablet, a gelatin encapsulation, or a powder.

22. A process for the preparation of a rapidly disintegrating solid dosage form capable of forming a stable suspension without irreversible particle aggregation, particle agglomeration or particle growth comprising the steps of:
   a) admixing at least two matrix-forming agents with an aqueous homogeneous suspension including solid drug particles onto which is adsorbed at least one surface stabilizing agent of which one is a phospholipid, or a combination of one or more surface stabilizing agents and one or more phospholipids, wherein the aqueous homogeneous suspension is prepared with a water insoluble or poorly water-soluble drug in the presence of one or more surface stabilizing agents, of which at least one is a phospholipid and is subjected to a particle fragmentation process resulting in a suspension of micron and submicron particles, wherein the mean volume weighted particle size of the water-insoluble or poorly water-soluble drug particles in the suspension ranges between about 0.05 and about 10 micrometers, and further wherein said at least two rapidly dispersible matrix-forming bulking/releasing agents, or said combination of matrix-forming bulking agent and matrix-forming releasing agent, are present in an amount of between 0.1% w/w and 90% w/w of the aqueous suspension, said amount permitting a dried solid form of said suspension, upon reconstitution in an aqueous environment, to revert to a suspension having no more than about 20% by weight of particle aggregation or agglomeration compared with the amount of aggregation or agglomeration of particles comprising a pre-dried suspension;
   b) distributing the admixture of step (a) into unit dosage form molds; and
   c) freeze-drying said admixture in said unit dosage form molds to produce a solid dosage form of the surface stabilized drug particles dispersed and embedded throughout a support matrix of said matrix-forming agent or agents, wherein said matrix dissolves or substantially disperses in a rapid disintegration time of less than 2 minutes upon contact with an aqueous environment to release the surface stabilized drug particles into the aqueous environment as a suspension; and further after contact between the solid and the aqueous environment, the resulting suspension comprises no more than 20% by weight of aggregated or agglomerated primary particles.

23. The process according to claim 22, wherein the at least two matrix-forming agents are selected from the group consisting of a pharmaceutically acceptable saccharide, a pharmaceutically acceptable polysaccharide; a pharmaceutically acceptable humectant a pharmaceutically acceptable cellulose based polymer, combinations thereof, and combinations of these with a pH buffering salt.

24. The process according to claim 22, wherein the at least two matrix-forming agents are selected from the group consisting of mannitol, trehalose, sorbitol, maltose, sucrose, lactose and combinations thereof; combinations of mannitol, trehalose, sorbitol and maltose with lactose; combinations of mannitol, trehalose, sorbitol, maltose and lactose with sucrose; microcrystalline cellulose, hydroxymethyl cellulose, hydroxypropyl cellulose, methylcellulose and combinations thereof; and combinations thereof with a pH buffering salt.

25. The process according to claim 22, wherein the at least two matrix-forming agents are present in an amount between 0.5% w/w and 50% w/w of the aqueous suspension.

26. The process according to claim 22, wherein the water insoluble or poorly water-soluble drug is selected from the group consisting of antifungal agents, immunosuppressive agents, immunoactive agents, antiviral agents, antineoplastic agents, analgesic agents, anti-inflammatory agents, antibiotic agents, antiepileptic agents, anesthetic agents, hypnotic agents, sedative agents, antipsychotic agents, neuroleptic agents, antidepressant agents, anxiolytic agents, anticonvulsant agents, antagonist agents, neuron blocking agents, anticholinergic agents, cholinomimetic agents, antimuscarinic agents, muscarinic agents, anti adrenergic agents, antiarrhythmic agents, antihypertensive agents, hormones, and nutrients.

27. The process according to claim 22, wherein the drug is fenofibrate, itraconazole, or cyclosporine.

28. The process according to claim 22, wherein the drug is present in an amount between 0.1% w/w and 60% w/w of the aqueous suspension.

29. The process according to claim 22, wherein the phospholipid is selected from the group consisting of an egg phospholipid, a soybean phospholipid, and combinations thereof.

30. The process according to claim 22, wherein the phospholipid is selected from the group consisting of hydrogenated phospholipid, partially hydrogenated phospholipid, and combinations thereof.

31. The process according to claim 22, wherein the phospholipid is selected from the group consisting of phosphatidylcholine, phosphatidylethanolamine, phosphatidylserine, phosphatidylinositol, phosphatidylglycerol, phosphatidic acid, a lysophospholipid, and combinations thereof.

32. The process according to claim 22, wherein the surface modifying agent is selected from the group consisting of pharmaceutically acceptable nonionic surfactants, pharmaceutically acceptable anionic surfactants, and pharmaceutically acceptable cationic surfactants.

33. The process according to claim 22, wherein the surface modifying agent is selected from the group consisting of casein, gelatin, tragacanth, acacia, and combinations thereof.

34. The process according to claim 22, wherein the surface modifying agent is selected from the group consisting of a pharmaceutically acceptable polyoxyethylene fatty alcohol ether, a sorbitan fatty acid ester, a polyoxyethylene fatty acid ester, a poloxamer, a polaxamine, and combinations thereof.

35. The process according to claim 22, wherein the surface modifying agent is selected from the group consisting of glycerol monostearate, cetyl alcohol, cetostearyl alcohol, stearyl alcohol, and combinations thereof.

36. The process according to claim 22, wherein the surface modifying agent is selected from the group consisting of potassium laurate, triethanolamine stearate, sodium lauryl sulfate, an alkyl polyoxyethylene sulfate, sodium alginate, sodium deoxycholate, dioctyl sodium sulfosuccinate, a negatively charged glyceryl ester, sodium carboxymethylcellulose, calcium carboxymethylcellulose, and combinations thereof.

37. The process according to claim 22, wherein the surface modifying agent is selected from the group consisting of benzalkonium chloride, cetyltrimethylammonium bromide, lauryldimethylbenzylammonium chloride, and combinations thereof.

38. The process according to claim 22, wherein the surface modifying agent is present in an amount between 0.5% w/w and 50% w/w of the aqueous suspension.

39. The process according to claim 22, wherein the particle fragmentation process is selected from the group consisting of sonication, milling, homogenization, micro fluidization, antisolvent precipitation and solvent precipitation.

40. The process according to claim 22, wherein the dosage form is a tablet.

41. A dosage form prepared by the process of claim 1.

42. A dosage form prepared by the process of claim 22.

43. A process for the preparation of a rapidly disintegrating solid dosage form capable of forming a stable suspension without irreversible particle aggregation, particle agglomeration, or particle growth, comprising the steps of:
  a) preparing an aqueous suspension including a water insoluble or poorly water-soluble drug in the presence of one or more surface stabilizing agents, of which at least one is a phospholipid, or a combination of one or more surface stabilizing agents and one or more phospholipids, wherein the concentration of the phospholipid in the aqueous suspension ranges from about 0.1% w/w to about 90% w/w;
  b) admixing the aqueous suspension of step a) with at least two rapidly dispersible matrix-forming agents, said at least two rapidly dispersible matrix-forming agents, being present in an amount of between 0.1% w/w and 90% w/w of the aqueous suspension, said amount permitting a dried solid form of said suspension, upon reconstitution in an aqueous environment, to revert to a suspension having no more than about 20% by weight of particle aggregation or agglomeration compared with the amount of aggregation or agglomeration of particles comprising a pre-dried suspension;
  c) subjecting the aqueous suspension to a particle fragmentation process to form a homogeneous aqueous suspension of micron and submicron particles, wherein the mean volume weighted particle size of the water-insoluble or poorly water-soluble drug particles in the suspension ranges between about 0.05 and about 10 micrometers;
  d) drying the homogeneous suspension of step c) to produce a solid having surface stabilized drug particles dispersed and embedded throughout a support matrix formed by the at least two matrix-forming agents, or combination thereof;
  wherein the support matrix dissolves or substantially disperses in a rapid disintegration time of less than 2 minutes upon contact between the solid and aqueous environment resulting in a release of the surface stabilized drug particles into the aqueous environment as a suspension; and further wherein, after contact between the solid and the aqueous environment, the resulting suspension comprises no more than 20% by weight of aggregated or agglomerated primary particles;
  e) optionally course milling and blending the solid with one or more pharmaceutically acceptable excipients to produce a dried powder; and
  f) forming the solid or dried powder into a solid dosage form of the drug.

44. A process for the preparation of a rapidly disintegrating solid dosage form capable of forming a stable suspension without irreversible particle aggregation, particle agglomeration, or particle growth, comprising the steps of:
  a) preparing an aqueous suspension including a water insoluble or poorly water-soluble drug selected from the group consisting of cyclosporine, itraconazole and fenofibrate, in the presence of one or more surface stabilizing agents selected from the group consisting of Myrj™52, polyvinyl pyrrolidone (PVP 17), sodium deoxycholate, TWEEN™80 and a combination thereof, and further including at least one phospholipid selected from the group consisting of phosphatidylcholine, phosphatidylethanolamine, phosphatidylserine, phosphatidylinositol, phosphatidylglycerol, phosphatidic acid, a lysophospholipid, and combinations thereof; wherein the concentration of the phospholipid in the aqueous suspension ranges from about 0.1% w/w to about 90% w/w;
  b) subjecting the aqueous suspension of step a) to a particle fragmentation process to form a homogeneous aqueous suspension of micron and submicron particles, wherein the mean volume weighted particle size of the water-insoluble or poorly water-soluble drug particles in the suspension ranges between about 0.05 and about 10 micrometers;
  c) admixing the homogenous suspension of step b) with at least two rapidly dispersible matrix-forming agents, said at least two matrix-forming agents selected from the group consisting of sucrose, lactose, trehalose, mannitol, sorbitol and a combination thereof, said at least two rapidly dispersible matrix-forming agents, being present in an amount of between 0.1% w/w and 90% w/w of the aqueous suspension, said amount permitting a dried solid form of said suspension, upon reconstitution in an aqueous environment, to revert to a suspension having no more than about 20% by weight of particle aggregation or agglomeration compared with the amount of aggregation or agglomeration of particles comprising a pre-dried suspension;
  d) drying the admixture to produce a solid having surface stabilized drug particles dispersed and embedded throughout a support matrix formed by the at least two matrix-forming bulking/releasing agents, or combination thereof;
  wherein the support matrix dissolves or substantially disperses in a rapid disintegration time of less than 2 minutes upon contact between the solid and aqueous environment resulting in a release of the surface stabilized drug particles into the aqueous environment as a suspension; and further wherein, after contact between the solid and the aqueous environment, the resulting suspension comprises no more than 20% by weight of aggregated or agglomerated primary particles;
  e) optionally course milling and blending the solid with one or more pharmaceutically acceptable excipients to produce a dried powder; and
  f) forming the solid or dried powder into a solid dosage form of the drug.

45. The process according to any one of claims 1, 22, 43, or 44, wherein, in step d), said reconstituted suspension comprises no more than 10% by weight of aggregated primary particles.

46. The process according to any one of claims 1, 22, 43, or 44, wherein, in step d), said reconstituted suspension comprises no more than 1% by weight of aggregated primary particles.

47. A dosage form prepared by the process of claim 43.

48. A dosage form prepared by the process of claim 44.

49. The process according to claim 43, wherein the at least two matrix-forming agents are selected from the group consisting of a pharmaceutically acceptable saccharide, a pharmaceutically acceptable polysaccharide, a pharmaceutically acceptable humectant, a pharmaceutically acceptable cellulose based polymer, combinations thereof, and combinations of these with a pH buffering salt.

50. The process according to claim 1, wherein the at least two matrix-forming agents are selected from the group consisting of mannitol, trehalose, sorbitol, maltose and combinations thereof; combinations of mannitol, trehalose, sorbitol and maltose with lactose; combinations of mannitol, trehalose, sorbitol, maltose, and lactose with sucrose; microcrystalline cellulose, hydroxymethyl cellulose, hydroxypropyl cellulose, methylcellulose and combinations thereof; and combinations thereof with a pH buffering salt.

51. The process according to claim 43, wherein the water-insoluble or poorly water-soluble drug is selected from the group consisting of antifungal agents, immunosuppressive agents, immunoactive agents, antiviral agents, antineoplastic agents, analgesic agents, anti-inflammatory agents, antibiotic agents, antiepileptic agents, anesthetic agents, hypnotic agents, sedative agents, antipsychotic agents, neuroleptic agents, antidepressant agents, anxiolytic agents, anticonvulsant agents, antagonist agents, neuron blocking agents, anticholinergic agents, cholinomimetic agents, antimuscarinic agents, muscarinic agents, anti adrenergic agents, antiarrhythmic agents, antihypertensive agents, hormones, and nutrients.

52. The process according to claim 43, wherein the drug is selected from the group consisting of fenofibrate, itraconazole, and cyclosporine.

53. The process according to claim 43 or claim 44, wherein the drug is present in an amount between 0.1% w/w and 60% w/w of the aqueous suspension.

54. The process according to claim 43, wherein the phospholipid is selected from the group consisting of an egg phospholipid, a soybean phospholipid, and combinations thereof.

55. The process according to claim 43, wherein the phospholipid is selected from the group consisting of hydrogenated phospholipid, partially hydrogenated phospholipid, and combinations thereof.

56. The process according to claim 43, wherein the phospholipid is selected from the group consisting of phosphatidylcholine, phosphatidylethanolamine, phosphatidylserine, phosphatidylinositol, phosphatidylglycerol, phosphatidic acid, a lysophospholipid, and combinations thereof.

57. The process according to claim 43, wherein the surface stabilizing agent is selected from the group consisting of pharmaceutically acceptable nonionic surfactants, pharmaceutically acceptable anionic surfactants, and pharmaceutically acceptable cationic surfactants.

58. The process according to claim 43, wherein the surface stabilizing agent is selected from the group consisting of casein, gelatin, tragacanth, acacia, and combinations thereof.

59. The process according to claim 43, wherein the surface stabilizing agent is selected from the group consisting of a pharmaceutically acceptable polyoxyethylene fatty alcohol ether, a sorbitan fatty acid ester, a polyoxyethylene fatty acid ester, a poloxamer, a polaxamine, and combinations thereof.

60. The process according to claim 43, wherein the surface stabilizing agent is selected from the group consisting of glycerol monostearate, cetyl alcohol, cetostearyl alcohol, stearyl alcohol, and combinations thereof.

61. The process according to claim 43, wherein the surface stabilizing agent is selected from the group consisting of potassium laurate, triethanolamine stearate, sodium lauryl sulfate, an alkyl polyoxyethylene sulfate, sodium alginate, sodium deoxycholate, dioctyl sodium sulfosuccinate, a negatively charged glyceryl ester, sodium carboxymethylcellulose, calcium carboxymethylcellulose, and combinations thereof.

62. The process according to claim 43, wherein the surface stabilizing agent is selected from the group consisting of benzalkonium chloride, cetyltrimethylammonium bromide, lauryldimethylbenzylammonium chloride, and combinations thereof.

63. The process according to claim 43, wherein the surface stabilizing agent is present in an amount between 0.5% w/w and 50% w/w of the aqueous suspension.

64. The process according to claim 43 or claim 44, wherein, in step d), the admixture is dried by spray drying, spray coating, or freeze-drying.

65. The process according to claim 43 or claim 44, wherein the particle fragmentation process is selected from the group consisting of sonication, milling, homogenization, microfluidization, antisolvent precipitation and solvent precipitation.

66. The process according to claim 43 or claim 44, wherein the pharmaceutically acceptable excipient is a tableting aid for compression, a glidant for hard gelatin encapsulation, an effervescent disintegration agent, a dispersant for a dry powder inhaler, or a combination thereof.

67. The process according to claim 43 or claim 44, wherein the dosage form is a tablet, a gelatin encapsulation, or a powder.

68. The process according to claim 1, wherein, in step c), said suspension has no more than about 10% by weight of particle aggregation or agglomeration compared with the amount of aggregation or agglomeration of particles comprising a pre-dried suspension.

69. The process according to claim 22, wherein, in step a), said suspension has no more than about 10% by weight of particle aggregation or agglomeration compared with the amount of aggregation or agglomeration of particles comprising a pre-dried suspension.

70. The process according to claim 43, wherein, in step b), said suspension has no more than about 10% by weight of particle aggregation or agglomeration compared with the amount of aggregation or agglomeration of particles comprising a pre-dried suspension.

71. The process according to claim 44 wherein, in step c), said suspension has no more than about 10% by weight of particle aggregation or agglomeration compared with the amount of aggregation or agglomeration of particles comprising a pre-dried suspension.

72. The process according to claim 6, wherein the drug is fenofibrate.

73. The process according to claim 27, wherein the drug is fenofibrate.

74. The process according to claim 52, wherein the drug is fenofibrate.

* * * * *

UNITED STATES PATENT AND TRADEMARK OFFICE
CERTIFICATE OF CORRECTION

| | | |
|---|---|---|
| PATENT NO. | : 7,939,105 B2 | Page 1 of 1 |
| APPLICATION NO. | : 09/443863 | |
| DATED | : May 10, 2011 | |
| INVENTOR(S) | : Indu Parikh et al. | |

It is certified that error appears in the above-identified patent and that said Letters Patent is hereby corrected as shown below:

Column 11, line 19, claim 19, the phrase "sonication. milling, homogenization,..." should read --sonication, milling, homogenization.......--.

Signed and Sealed this
Fourteenth Day of June, 2011

David J. Kappos
*Director of the United States Patent and Trademark Office*